US009255877B2

(12) United States Patent
Veldman et al.

(10) Patent No.: US 9,255,877 B2
(45) Date of Patent: Feb. 9, 2016

(54) METROLOGY SYSTEM OPTIMIZATION FOR PARAMETER TRACKING

(71) Applicant: KLA-Tencor Corporation, Milpitas, CA (US)

(72) Inventors: Andrei Veldman, Sunnyvale, CA (US); Andrei V. Shchegrov, Campbell, CA (US); Gregory Brady, San Jose, CA (US); Thaddeus Gerard Dziura, San Jose, CA (US); Stilian Ivanov Pandev, Santa Clara, CA (US); Alexander Kuznetsov, Mountain View, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 14/278,224

(22) Filed: May 15, 2014

(65) Prior Publication Data

US 2014/0347666 A1    Nov. 27, 2014

Related U.S. Application Data

(60) Provisional application No. 61/825,814, filed on May 21, 2013.

(51) Int. Cl.
*G01N 21/21* (2006.01)
*G01N 21/95* (2006.01)
*G01B 11/06* (2006.01)

(52) U.S. Cl.
CPC .......... *G01N 21/211* (2013.01); *G01B 11/0625* (2013.01); *G01B 11/0641* (2013.01); *G01N 21/9501* (2013.01); *G01B 2210/56* (2013.01); *G01N 2021/213* (2013.01)

(58) Field of Classification Search
CPC ............ G01N 21/211; G01N 21/9501; G01N 2021/213

USPC .......... 356/366–369, 600–636; 702/196, 189; 700/108, 81, 96.96
See application file for complete search history.

(56) References Cited

U.S. PATENT DOCUMENTS 7,395,132 B2 * 7/2008 Prager et al. .................. 700/108
7,478,019 B2    1/2009 Zangooie et al.
(Continued)

FOREIGN PATENT DOCUMENTS

JP    2007329337    12/2007

OTHER PUBLICATIONS

International Search Report and Written Opinion mailed on Sep. 17, 2014, for PCT Application No. PCT/US2014/038643 filed on May 19, 2014, by KLA-Tencor Corporation, 10 pages.

*Primary Examiner* — Sang Nguyen
(74) *Attorney, Agent, or Firm* — Spano Law Group; Joseph S. Spano

(57) ABSTRACT

Methods and systems for evaluating the capability of a measurement system to track measurement parameters through a given process window are presented herein. Performance evaluations include random perturbations, systematic perturbations, or both to effectively characterize the impact of model errors, metrology system imperfections, and calibration errors, among others. In some examples, metrology target parameters are predetermined as part of a Design of Experiments (DOE). Estimated values of the metrology target parameters are compared to the known DOE parameter values to determine the tracking capability of the particular measurement. In some examples, the measurement model is parameterized by principal components to reduce the number of degrees of freedom of the measurement model. In addition, exemplary methods and systems for optimizing the measurement capability of semiconductor metrology systems for metrology applications subject to process variations are presented.

20 Claims, 11 Drawing Sheets

(56) References Cited

U.S. PATENT DOCUMENTS

| | | | |
|---|---|---|---|
| 8,666,703 B2* | 3/2014 | Ferns et al. | 703/1 |
| 8,879,073 B2* | 11/2014 | Madsen et al. | 356/625 |
| 2007/0225851 A1* | 9/2007 | Prager et al. | 700/108 |
| 2011/0246141 A1 | 10/2011 | Li | |
| 2012/0022836 A1 | 1/2012 | Ferns et al. | |
| 2012/0116733 A1 | 5/2012 | Thattaisundaram et al. | |
| 2013/0222795 A1 | 8/2013 | Madsen et al. | |
| 2013/0262044 A1 | 10/2013 | Pandev et al. | |
| 2014/0297211 A1* | 10/2014 | Pandev et al. | 702/81 |
| 2014/0316730 A1* | 10/2014 | Shchegrov et al. | 702/81 |

* cited by examiner

| | PROCESS CORRELATIONS | | |
|---|---|---|---|
| | H | SWA | CD |
| H | | -0.97 | 0.94 |
| SWA | | | -1.00 |
| CD | | | |

| | PROCESS CORRELATIONS | |
|---|---|---|
| | FOCUS | EXPOSURE |
| FOCUS | | -0.82 |
| EXPOSURE | | |

METROLOGY SYSTEM OPTIMIZATION FOR PARAMETER TRACKING

CROSS REFERENCE TO RELATED APPLICATION

The present application for patent claims priority under 35 U.S.C. §119 from U.S. provisional patent application Ser. No. 61/825,814, entitled "Method And Apparatus For Characterization And Optimization Of Measurement Performance and Parameter Tracking For A Metrology System In The Presence Of Systematic And Random Perturbations," filed May 21, 2013, the subject matter of which is incorporated herein by reference in its entirety.

TECHNICAL FIELD

The described embodiments relate to metrology systems and methods, and more particularly to methods and systems for improved parameter measurement.

BACKGROUND INFORMATION

Semiconductor devices such as logic and memory devices are typically fabricated by a sequence of processing steps applied to a specimen. The various features and multiple structural levels of the semiconductor devices are formed by these processing steps. For example, lithography among others is one semiconductor fabrication process that involves generating a pattern on a semiconductor wafer. Additional examples of semiconductor fabrication processes include, but are not limited to, chemical-mechanical polishing, etch, deposition, and ion implantation. Multiple semiconductor devices may be fabricated on a single semiconductor wafer and then separated into individual semiconductor devices.

Metrology processes are used at various steps during a semiconductor manufacturing process to detect defects on wafers to promote higher yield. Optical metrology techniques offer the potential for high throughput without the risk of sample destruction. A number of optical metrology based techniques including scatterometry and reflectometry implementations and associated analysis algorithms are commonly used to characterize critical dimensions, film thicknesses, composition and other parameters of nanoscale structures.

Traditionally, optical metrology is performed on targets consisting of thin films and/or repeated periodic structures. During device fabrication, these films and periodic structures typically represent the actual device geometry and material structure or an intermediate design. As devices (e.g., logic and memory devices) move toward smaller nanometer-scale dimensions, characterization becomes more difficult. Devices incorporating complex three-dimensional geometry and materials with diverse physical properties contribute to characterization difficulty.

For example, modern memory structures are often high-aspect ratio, three-dimensional structures that make it difficult for optical radiation to penetrate to the bottom layers. In addition, the increasing number of parameters required to characterize complex structures (e.g., FinFETs), leads to increasing parameter correlation. As a result, the measurement model parameters characterizing the target often cannot be reliably decoupled.

In response to these challenges, more complex optical tools and signal processing computer algorithms have been developed. Measurements are performed over large ranges of several machine parameters (e.g., wavelength, azimuth and angle of incidence, etc.), and often simultaneously. As a result, the measurement time, computation time, and the overall time to generate reliable results, including measurement recipes, increases significantly.

In general, optical metrology techniques applicable to semiconductor structures are indirect methods of measuring physical properties of a metrology target. In most cases, the measured signals cannot be used to directly determine the physical properties of interest. Traditionally, the measurement process consists of formulating a metrology-based target model that attempts to predict the measured signals based on a model of the interaction of the measurement target with the particular metrology system. The metrology-based target model includes a parameterization of the structure in terms of the physical properties of the measurement target of interest (e.g., film thicknesses, critical dimensions, refractive indices, grating pitch, etc.). In addition, the metrology-based target model includes a parameterization of the measurement tool itself (e.g., wavelengths, angles of incidence, polarization angles, etc.).

System parameters are parameters used to characterize the metrology tool itself. Exemplary system parameters include angle of incidence (AOI), analyzer angle ($A_O$), polarizer angle ($P_O$), illumination wavelength, numerical aperture (NA), etc. Target parameters are parameters used to characterize the geometric and material properties of the metrology target. For a thin film specimen, exemplary target parameters include refractive index (or dielectric function tensor), nominal layer thickness of all layers, layer sequence, etc.

Traditionally, a metrology target is provided by a semiconductor device manufacturer. A metrology-based target model is constructed to simulate the geometry and materials of the metrology target and the interaction of the metrology target with one or more metrology systems, or subsystems. A measurement recipe is developed based on an analysis of simulated measurement signals derived from one or more metrology-based target models, each representative of an interaction between the metrology target and a candidate metrology system, or subsystem (e.g., spectroscopic ellipsometers, etc.).

Traditionally, the formulation of the measurement recipe is guided by a sensitivity analysis of the simulated measurement signals. Some examples include an analysis of the derivatives of the simulated measurement signals (e.g., optical signals such as reflectivity) with respect to the target parameters of interest, analysis of parameter correlations, and a prediction of measurement precision in the presence of random temporal noise. The most common approach to assess and optimize metrology systems is based on a 1st order perturbation approach. In this approach, normally distributed random noise affecting the measured signal is translated into an uncertainty of the parameters measured by the metrology system. The estimated parameter uncertainty resulting from the random noise (i.e., measurement parameter precision) is typically used as the main figure of merit for metrology system performance and recipe optimization. This estimate of measurement system precision is typically expressed as a three-sigma value (i.e., a value that is three times the standard deviation of the estimated distribution of parameter values). Optimization and development of a measurement recipe is typically targeted toward improving the expected measurement precision. Some examples are described by J. Ferns et al., in U.S. Patent Publication No. 2012/0022836, "Method for Automated Determination of an Optimally Parameterized Scatterometry Model," the subject matter of which is incorporated herein by reference in its entirety. Other examples are described by R. Silver et al., in "Fundamental Limits of Optical Critical Dimension Metrology: A Simulation Study," published in the Proc. of SPIE, Vol. 6518, 65180U, (2007), the subject matter of which is incorporated herein by reference in its entirety.

However, the emphasis on measurement precision as the main figure of merit for optimization limits the effectiveness of the resulting measurement recipe. Recent improvements in light sources, detectors, and stability of metrology components have enabled measurements with a high level of precision (i.e., low three-sigma values), but the ability to track variations of measured parameters through a process window remains elusive.

Reliance on first order analyses of random temporal noise perturbations (e.g., multi-dimensional Taylor series expansions to first order) results in reasonably accurate predictions in a measurement scenario where measurement signal perturbations (random or systematic) are small compared to measurement signal variation due to changes in the measured parameters induced by the manufacturing process. But, if the actual measurement scenario does not comport with this assumption, a first order perturbation analysis may produce erroneous performance predictions. This may occur, for example, in a measurement scenario with low sensitivity and large perturbations, or when multiple perturbations affect the system simultaneously. As a result, a measurement recipe optimized for precision based on a first order perturbation analysis may lead to a metrology tool that reports inaccurate results with seemingly satisfactory precision. This is often evidenced by comparing results of model-based optical measurements and measurements from a trusted reference measurement system such as transmission electron microscope (TEM).

Future metrology applications present challenges for metrology due to increasingly small resolution requirements, multi-parameter correlation, increasingly complex geometric structures, and increasing use of opaque materials. It is becoming more important to track process-induced parameter variations, such as CD or film thickness variations, and the lack of parameter tracking capability is a serious challenge. Thus, methods and systems for improved measurements are desired.

SUMMARY

Methods and systems for evaluating the capability of a measurement system to track measurement parameters through a given process window are described herein. In addition, exemplary methods and systems for optimizing the measurement capability of semiconductor metrology systems for critical dimension, film thickness, and composition metrology applications subject to process variations are presented.

In one aspect, simulation and analysis of precision, accuracy, and process tracking of measurement model parameters of interest is performed in the presence systematic errors. Such errors include model errors, metrology system imperfections, and calibration errors, among others. In this manner, the real-world capability of a particular measurement system measuring a particular metrology target is evaluated. Performance evaluations include at least one systematic or random perturbation, and in some examples, multiple, simultaneous perturbations, including both random and systematic perturbations.

In some examples, the values of particular metrology target parameters are pre-determined as part of a simulated Design of Experiments (DOE). Model-based metrology measurements are simulated and estimated values of the particular metrology target parameters are compared to the known DOE parameter values to determine the tracking capability of the particular measurement.

In some examples, metrology systems to measure and track one or more critical dimensions, thin film thicknesses, optical properties, material composition, overlay, lithography focus and dose, etc. are evaluated in accordance with the methods described herein.

In a further aspect, measurement capability is optimized based on the analysis. In this manner measurement capability can be evaluated, optimized, and confirmed for tracking process parameters such as focus and exposure in lithography, etch time, and other relevant process parameters without an independent, and much more accurate, reference measurement technology.

In some examples, one or more metrics indicative of parameter tracking performance or precision are evaluated to determine whether changes to the measurement model, measurement targets, metrology system, or combination of metrology systems are required to improve parameter tracking performance.

In another further aspect, the measurement model is parameterized by a process based principal component analysis (PCA) parameterization. In some examples, a PCA parameterization effectively reduces the number of degrees of freedom of the measurement model such that the model parameters can be effectively resolved from measurement data without excessive loss of measurement information.

In another further aspect, the methods and systems for evaluating the capability of a measurement system to track measurement parameters through a given process window as described herein are also applied to track process parameters of interest.

The foregoing is a summary and thus contains, by necessity, simplifications, generalizations and omissions of detail; consequently, those skilled in the art will appreciate that the summary is illustrative only and is not limiting in any way. Other aspects, inventive features, and advantages of the devices and/or processes described herein will become apparent in the non-limiting detailed description set forth herein.

DETAILED DESCRIPTION

Reference will now be made in detail to background examples and some embodiments of the invention, examples of which are illustrated in the accompanying drawings.

Methods and systems for evaluating the capability of a measurement system to track measurement parameters through a given process window are described herein. In addition, exemplary methods and systems for optimizing the measurement capability of semiconductor metrology systems for critical dimension, film thickness, and composition metrology applications subject to process variations are presented.

In one aspect, simulation and analysis of precision, accuracy, and process tracking of measurement model parameters of interest is performed in the presence systematic errors. Such errors include model errors, metrology system imperfections, and calibration errors, among others. In this manner, the real-world capability of a particular measurement system measuring a particular metrology target is evaluated.

Performance evaluations include at least one systematic or random perturbation, and in some examples, multiple, simultaneous perturbations, including both random and systematic perturbations. In addition, in some embodiments, the values of particular metrology target parameters are pre-determined as part of a simulated Design of Experiments (DOE). Model-based metrology measurements are simulated and estimated values of the particular metrology target parameters are compared to the known DOE parameter values to determine the tracking capability of the particular measurement.

In some examples, metrology systems to measure and track one or more critical dimensions, thin film thicknesses, optical properties, material composition, overlay, lithography focus and dose, etc. are evaluated in accordance with the methods described herein.

In a further aspect, measurement capability is optimized based on the analysis. In this manner measurement capability can be evaluated, optimized, and confirmed for tracking process parameters such as focus and exposure in lithography, etch time, and other relevant process parameters without an independent, and much more accurate, reference measurement technology.

In some examples, one or more metrics indicative of parameter tracking performance or precision are evaluated to determine whether changes to the measurement model, measurement targets, metrology system, or combination of metrology systems are required to improve parameter tracking performance.

Figure 1:
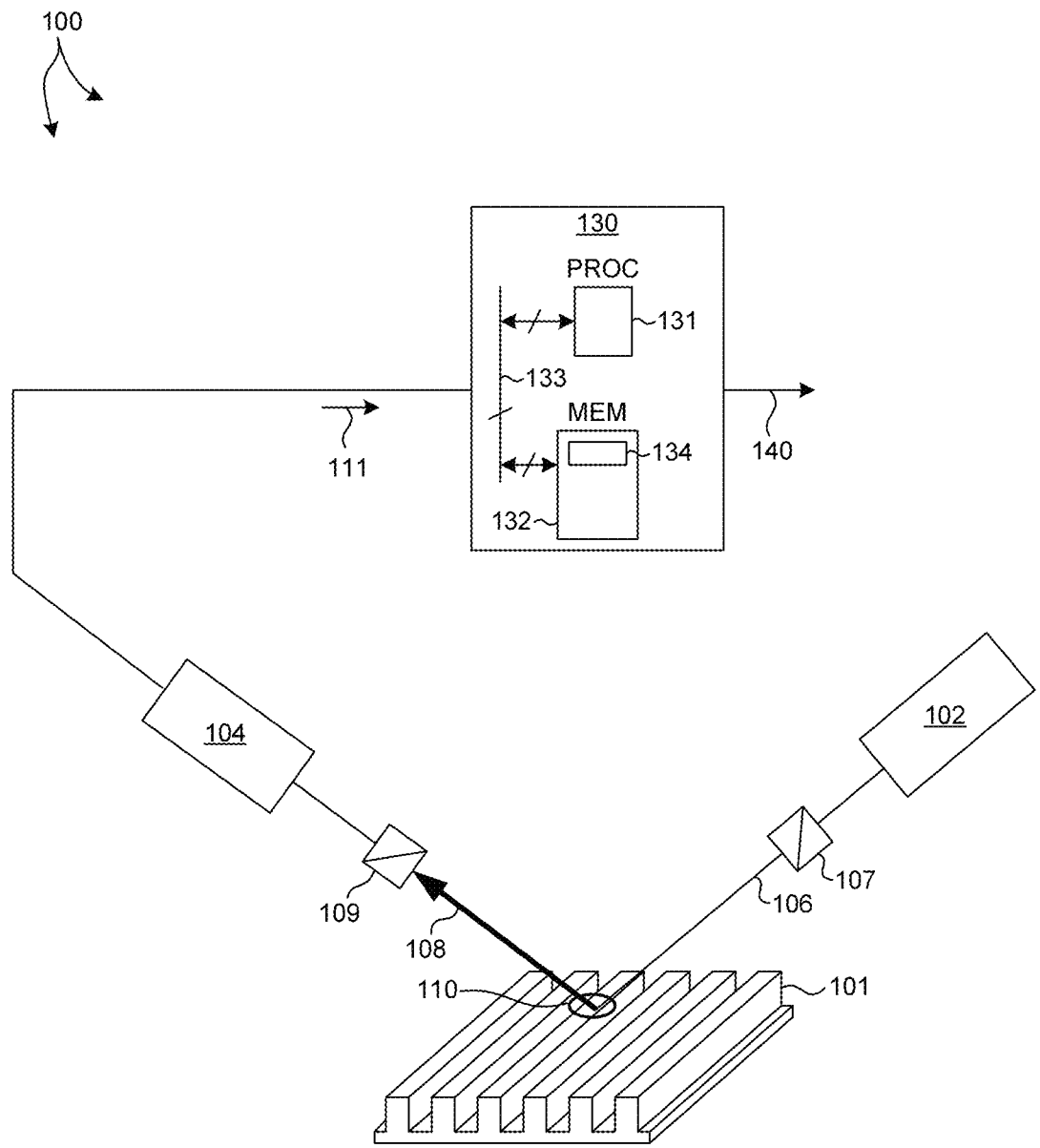
FIG. 1 is a diagram illustrative of a system 100 for evaluating and optimizing the capability of a measurement system to track measurement parameters through a given process window in accordance with the exemplary methods presented herein.

FIG. 1 illustrates a system 100 for measuring characteristics of a specimen in accordance with the exemplary methods presented herein. As shown in FIG. 1, the system 100 may be used to perform spectroscopic ellipsometry measurements of one or more structures of a specimen 101. In this aspect, the system 100 may include a spectroscopic ellipsometer equipped with an illuminator 102 and a spectrometer 104. The illuminator 102 of the system 100 is configured to generate and direct illumination of a selected wavelength range (e.g., 150-850 nm) to the structure disposed on the surface of the specimen 101. In turn, the spectrometer 104 is configured to receive illumination reflected from the surface of the specimen 101. It is further noted that the light emerging from the illuminator 102 is polarized using a polarization state generator 107 to produce a polarized illumination beam 106. The radiation reflected by the structure disposed on the specimen 101 is passed through a polarization state analyzer 109 and to the spectrometer 104. The radiation received by the spectrometer 104 in the collection beam 108 is analyzed with regard to polarization state, allowing for spectral analysis by the spectrometer of radiation passed by the analyzer. These spectra 111 are passed to the computing system 130 for analysis of the structure.

As depicted in FIG. 1, system 100 includes a single measurement technology (i.e., SE). However, in general, system 100 may include any number of different measurement technologies. By way of non-limiting example, system 100 may be configured as a spectroscopic ellipsometer (including Mueller matrix ellipsometry), a spectroscopic reflectometer, a spectroscopic scatterometer, an overlay scatterometer, an angular resolved beam profile reflectometer, a polarization resolved beam profile reflectometer, a beam profile reflectometer, a beam profile ellipsometer, any single or multiple wavelength ellipsometer, or any combination thereof. Furthermore, in general, measurement data collected by different measurement technologies and analyzed in accordance with the methods described herein may be collected from multiple tools, rather than one tool integrating multiple technologies.

In a further embodiment, system 100 may include one or more computing systems 130 employed to perform measurement based on an integrated measurement model in accordance with the methods described herein. The one or more computing systems 130 may be communicatively coupled to the spectrometer 104. In one aspect, the one or more computing systems 130 are configured to receive measurement data 111 associated with measurements of the structure of specimen 101.

In a further embodiment, the one or more computing systems 130 are configured to access model parameters in real-time, employing Real Time Critical Dimensioning (RTCD), or it may access libraries of pre-computed models for determining a measurement model in accordance with the methods described herein.

It should be recognized that the various steps described throughout the present disclosure may be carried out by a single computer system 130 or, alternatively, a multiple computer system 130. Moreover, different subsystems of the system 100, such as the spectroscopic ellipsometer 104, may include a computer system suitable for carrying out at least a portion of the steps described herein. Therefore, the aforementioned description should not be interpreted as a limitation on the present invention but merely an illustration. Further, the one or more computing systems 130 may be configured to perform any other step(s) of any of the method embodiments described herein.

In addition, the computer system 130 may be communicatively coupled to the spectrometer 104 in any manner known in the art. For example, the one or more computing systems 130 may be coupled to computing systems associated with the spectrometer 104. In another example, the spectrometer 104 may be controlled directly by a single computer system coupled to computer system 130.

The computer system 130 of the metrology system 100 may be configured to receive and/or acquire data or information from the subsystems of the system (e.g., spectrometer 104 and the like) by a transmission medium that may include wireline and/or wireless portions. In this manner, the transmission medium may serve as a data link between the computer system 130 and other subsystems of the system 100.

Computer system 130 of the integrated metrology system 100 may be configured to receive and/or acquire data or information (e.g., measurement results, modeling inputs, modeling results, etc.) from other systems by a transmission medium that may include wireline and/or wireless portions. In this manner, the transmission medium may serve as a data link between the computer system 130 and other systems (e.g., memory on-board metrology system 100, external memory, reference measurement source 120, or other external systems). For example, the computing system 130 may be configured to receive measurement data from a storage medium (i.e., memory 132 or an external memory) via a data link. For instance, spectral results obtained using spectrometer 104 may be stored in a permanent or semi-permanent memory device (e.g., memory 132 or an external memory). In this regard, the spectral results may be imported from on-board memory or from an external memory system. Moreover, the computer system 130 may send data to other systems via a transmission medium. For instance, a measurement model or a specimen parameter 140 determined by computer system 130 may be communicated and stored in an external memory. In this regard, measurement results may be exported to another system.

Computing system 130 may include, but is not limited to, a personal computer system, mainframe computer system, workstation, image computer, parallel processor, or any other device known in the art. In general, the term "computing system" may be broadly defined to encompass any device having one or more processors, including clusters of computers and/or computers containing Graphics Processing Units (GPU), which execute instructions from a memory medium.

Program instructions 134 implementing methods such as those described herein may be transmitted over a transmission medium such as a wire, cable, or wireless transmission link. For example, as illustrated in FIG. 1, program instructions 134 stored in memory 132 are transmitted to processor 131 over bus 133. Program instructions 134 are stored in a computer readable medium (e.g., memory 132). Exemplary computer-readable media include read-only memory, a random access memory, a magnetic or optical disk, or a magnetic tape.

Figure 2:
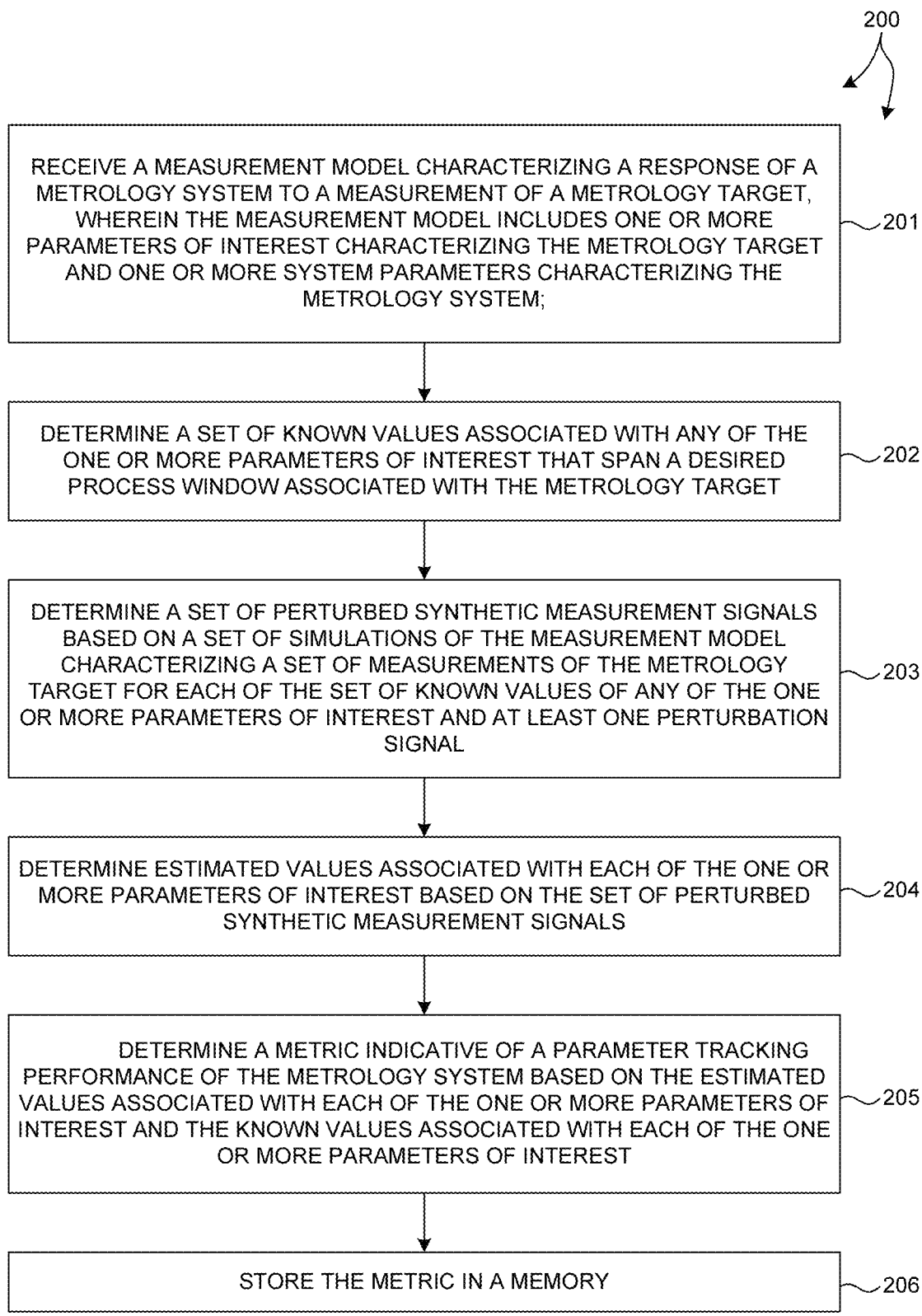
FIG. 2 is a flowchart illustrative of an exemplary method 200 suitable for implementation by the metrology system 100 of the present invention.

FIG. 2 illustrates a method 200 suitable for implementation by the metrology system 100 of the present invention. In one aspect, it is recognized that data processing blocks of method 200 may be carried out via a pre-programmed algorithm executed by one or more processors of computing system 130. While the following description is presented in the context of metrology system 100, it is recognized herein that the particular structural aspects of metrology system 100 do not represent limitations and should be interpreted as illustrative only.

In block 201, a measurement model characterizing a response of a metrology system to a measurement of a metrology target is received. By way of non-limiting example, the measurement model may be stored in memory 132 and received by processor 131 over bus 133. In another example, the measurement model may be stored on an external memory (not shown), and be imported by computing system 130. The measurement model includes one or more parameters of interest characterizing the metrology target and one or more system parameters characterizing the metrology system. The measurement model provides a parameterized, functional description of a structure to be measured by a metrology system. In general, the structure is represented by a model including N measurement parameters of interest (e.g. CD, film thicknesses, overlay, optical constants, focus and dose etc.), where N may be any integer value. However, in typical metrology applications, N is typically less than ten, and in many cases, less than five. The measurement model also provides a functional description of the metrology system characterized by system parameters such as wavelengths, polarizations, angles of incidence, etc., by way of non-limiting example.

The measurement model is used in solving what is sometimes referred to as a "direct" or "forward" problem. In other words, the measurement model can be used to compute an estimate of the raw measurement data (e.g., measurement spectra, speckle patterns, etc.) that would be generated by a measurement system measuring a target as specified by the choice of measurement model parameters used in the calculation. The solution of this problem is often termed as "direct" because the model can directly compute the estimated measurement data from the chosen parameter values without iteration. The problem of solving for expected measurement data as a function of the chosen parameter values is often described as the "forward" problem for the same reason. The measurement model is constructed to directly solve for the estimated measurement data by a forward computation.

In block 202, a set of known values associated with any of the one or more parameters of interest is determined. Each set of known values is selected to span a desired process window associated with the metrology target.

Each set of known values should span the desired process window in which parameter tracking is required. For a Design Of Experiments (DOE) scenario, the process window may be relatively large (e.g., a Focus-Exposure Matrix (FEM)). For typical production scenarios (sometimes called "CD Uniformity"), the process may be relatively small.

Figure 3:
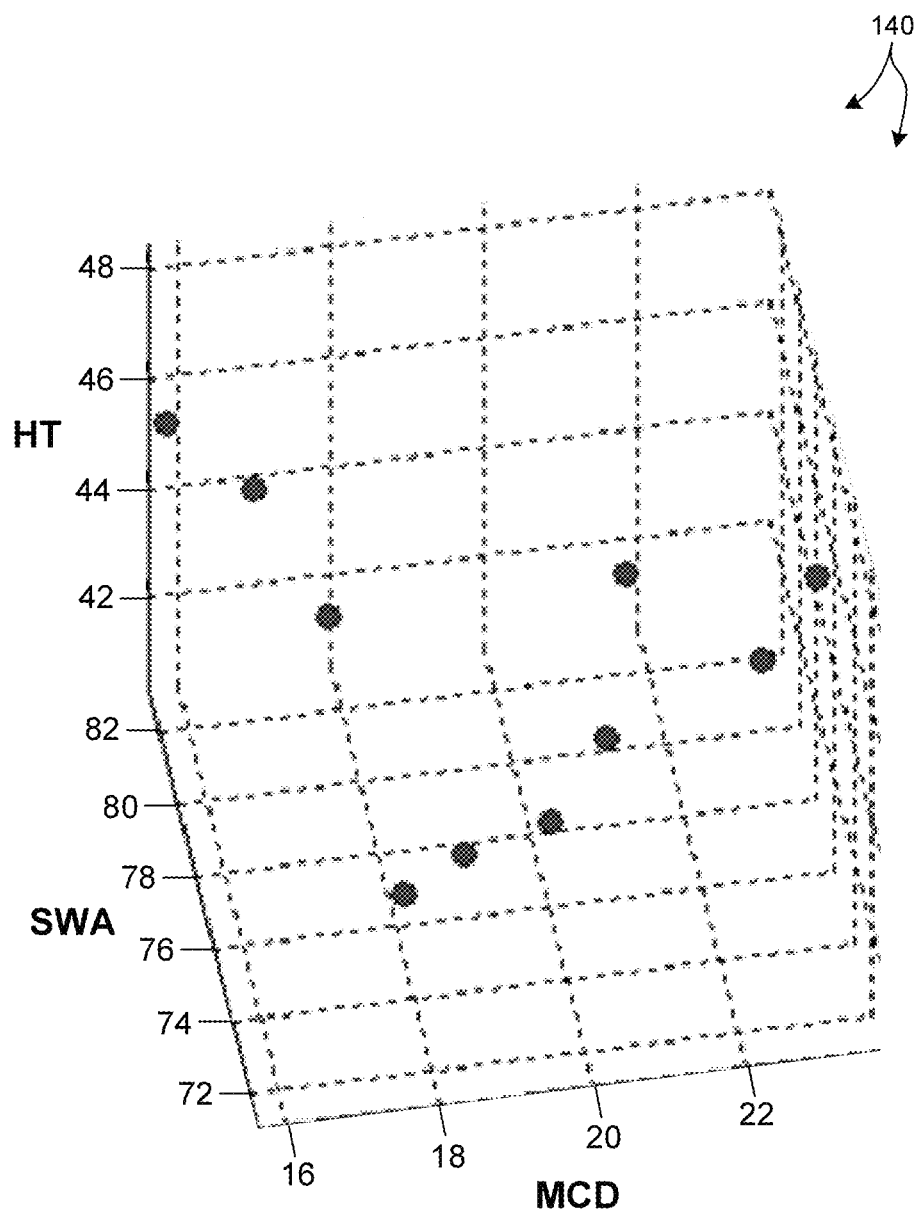
FIG. 3 illustrates a plot 210 showing three sets of pseudorandom values, corresponding to three parameters of interest of a metrology target, selected to simultaneously span a process window.

The distribution of known parameter values in the N-dimensional space of parameters of interest may be random, or quasi-random, to minimize the number of combinations to be tested, while still covering the entire process window. FIG. 3 illustrates a plot 210 showing three sets of values, corresponding to three parameters of interest. The three sets of values are selected to simultaneously span a process window for the three parameters of interest. In this example, the three parameters of interest are Middle Critical Dimension (MCD), Sidewall Angle (SWA), and Height (H) of a particular metrology target. In this example, a van der Corput sequence is employed to generate each of the sets of parameter values such that each one of the three parameters of interest uniformly covers the full expected range of each parameter with no apparent gaps, while the distribution still appears random. This example can be readily generalized to an arbitrary number of dimensions (i.e., an arbitrary number of parameters of interest) without significant additional computational cost. Although, a van der Corput sequence is illustrated, many other methods to generate sets of known parameter values that span the process window may be employed. For example, a quasi-normal distribution may be employed rather than a quasi-uniform distribution. In another example, a Cartesian grid of parameter values may be employed. Although, such a grid may incur a much greater computational cost.

In block 203, a set of perturbed synthetic measurement signals is determined based on a set of simulations of the measurement model characterizing a set of measurements of the metrology target for each of the set of known values of any of the one or more parameters of interest and at least one perturbation signal. In this manner, a set of simulated measurement signals is generated that spans the desired process window. Since the synthetic measurement signals are simulated, they are associated with known values of the measurement parameters of interest. For example, at each point in the N-dimensional space of measured parameters of interest, synthetic signals are generated that are indicative of the raw measurement signals that would be produced by the metrology system during actual measurements of the metrology target. In a preferred embodiment, the synthetic signals are generated by simulating the measurement model described with reference to block 201. In other words, the simulated signals are generated using the same solver used by the metrology system itself to produce realistic results. However, in some other embodiments, a different solver is employed to provide insight into the effect of systematic errors introduced by the solver itself.

In a further aspect, the perturbed synthetic measurement signals include the effects of known perturbations (i.e., systematic, random, or both). The perturbations may be systematic perturbations (e.g., static speckle, etc.), or random (e.g., temporal noise, etc.). The perturbations may apply to measurement model parameters such as metrology target model parameters and system. Perturbations may also apply to measured signals (e.g., based on measurement noise models).

In some examples, perturbations are the result of a separate simulation. For example, a simulation of speckle provides an estimate of a systematic perturbation (i.e., induced speckle) that can be added to simulated synthetic measurement signals to generate perturbed synthetic measurement signals. In another example, random noise perturbations may be numerically generated based on a noise model, and subsequently added to the simulated synthetic measurement signals to generate perturbed synthetic measurement signals. In some other examples, simulated systematic perturbations are an intrinsic part of the generation of the synthetic signals (e.g., a perturbation of the optical constants or geometric parameters during simulation).

In some other examples, systematic perturbations are extracted from experimentally measured data. In one such example, residual errors remaining at the end of a regression associated with a real measurement are extracted and then injected into the synthetically generated measurement signals to generate perturbed synthetic measurement signals. In another example, the asymmetrical portion of a real measured signal, which ideally should be symmetrical, is extracted and then injected into the synthetically generated measurement signals to generate perturbed synthetic measurement signals.

In some other examples, random perturbations are extracted from experimentally measured data and then added to the synthetically generated measurement signals to generate perturbed synthetic measurement signals.

In some other examples, perturbations are determined based on the differences between experimentally derived measurement signals from two or more metrology tools. These differences are added to the synthetically generated measurement signals to generate perturbed synthetic measurement signals. In this example, the set of perturbed synthetic measurement signals will include the effects of tool-to-tool matching performance.

In block 204, estimated values associated with each of the one or more parameters of interest are determined based on the set of perturbed synthetic measurement signals. In some embodiments, the perturbed synthetic signals are treated as measurement signals, and the metrology system runs its normal computational procedure and reports the estimated values of the parameters of interest.

The problem of estimating parameter values based on actual measurement data or perturbed synthetic measurement signals is often described as the "inverse" problem, or the "reverse" of the problem solved by the measurement model. In other words, the "inverse" of the measurement model can be used to compute an estimate of the values of the parameters of interest based on perturbed synthetic measurement data (e.g., synthetically generated measurement spectra, speckle patterns, etc.). Since it is often not possible to arrive at an analytical solution for the inverse of the measurement model, "indirect" methods such as recursion are often employed to arrive at a solution for parameter values based on perturbed synthetic measurement signals. In some embodiments, the solution procedure involves a non-linear regression on the underlying measurement model.

Although typically, the measurement procedure involves a non-linear regression on the underlying measurement model, in the special case of small systematic perturbations, a first order perturbation approach may be employed to reduce the computational burden.

Due to the additional perturbation effects added in block 203, the estimated measurement values of the parameters of interest will differ from the known values of the parameters of interest generated in block 202. These differences are the basis for parameter tracking through the process window.

In block 205, a metric indicative of a parameter tracking performance of the metrology system is determined. The metric is determined based on the known and estimated values associated with each of the one or more parameters of interest. In some examples, parameter tracking performance is evaluated by comparing the estimated values of the parameters of interest with the pre-defined, known values of the parameters of interest defined in block 202. Based on this comparison, the ability of the measurement system to track changes in the metrology target due to process-induced variations is evaluated, including the effects of systematic and random perturbations.

Figure 4A:
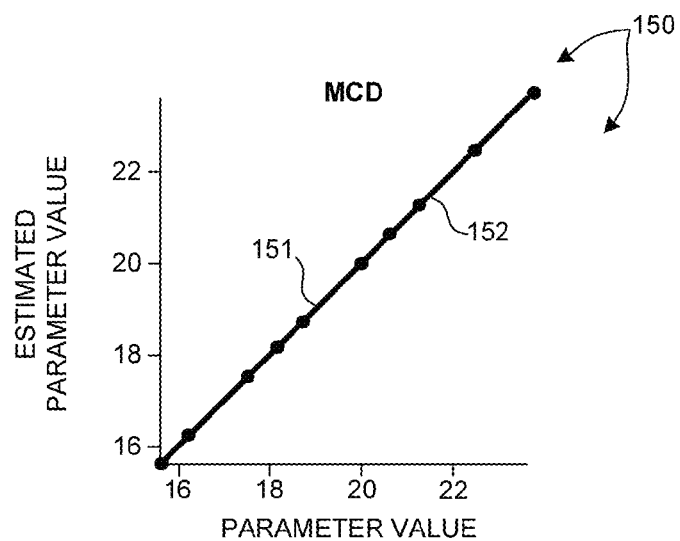
FIG. 4A depicts a linear fit of the estimated values of middle critical dimension (MCD) over a process window for a relatively low perturbation level.
Figure 4B:
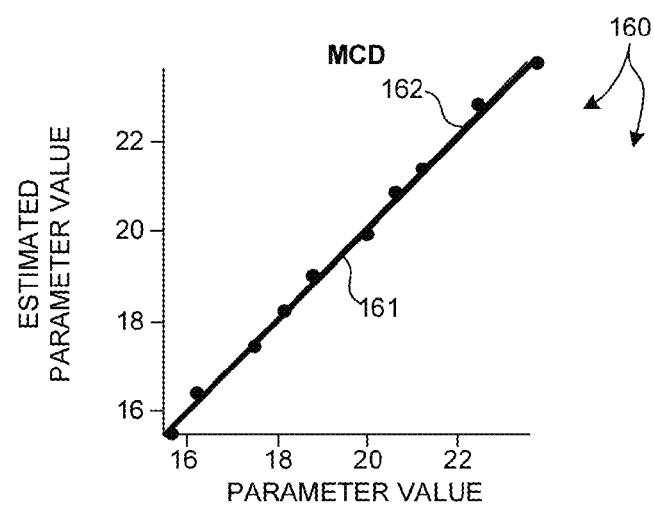
FIG. 4B depicts a linear fit of the estimated values of middle critical dimension (MCD) over a process window for a relatively moderate perturbation level.
Figure 4C:
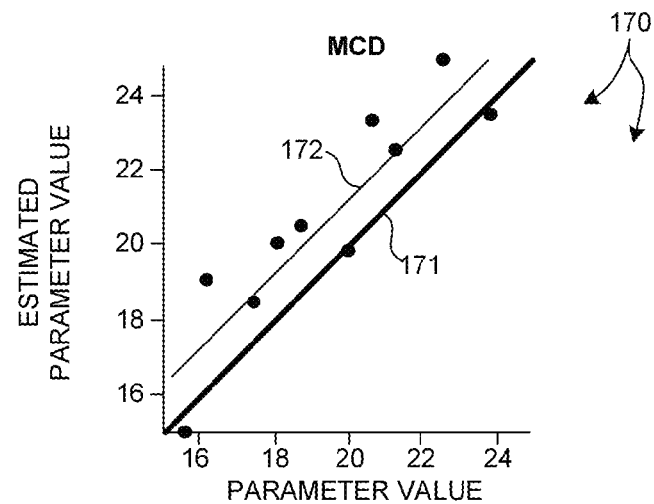
FIG. 4C depicts a linear fit of the estimated values of middle critical dimension (MCD) over a process window for a relatively high perturbation level.

By way of non-limiting example, the square of Pearson's correlation coefficient for linear regression, $R^2$, the slope of the linear fit, and the average offset of the linear fit between the estimated values of the parameters of interest with the known values of the parameters of interest are employed to characterize parameter tracking performance. FIGS. 4A-4C depict linear fits of the estimated values of a parameter of interest (MCD) over a process window for three different perturbation levels, respectively. The horizontal axes include the known values of each respective parameter of interest. The vertical axes include the estimated values of the parameters of interest with perturbations. To characterize how well estimated parameter values track through a process window, a straight line is fit to the plot of estimated parameter values versus known, simulated parameter values.

FIG. 4A depicts a plot 150 illustrating the linear fit 151 of the estimated values of MCD for a relatively small perturbation level. For reference, line 152 illustrates a perfect fit to the known parameter values. FIG. 4B depicts a plot 160 illustrating the linear fit 161 of the estimated values of MCD for a larger perturbation level than that depicted in FIG. 4A. For reference, line 162 illustrates a perfect fit to the known parameter values. FIG. 4C depicts a plot 170 illustrating the linear fit 171 of the estimated values of MCD for a larger perturbation level than that depicted in FIG. 4B. For reference, line 172 illustrates a perfect fit to the known parameter values. As illustrated in FIGS. 4A-4B, as the perturbation level increases the capability of the measurement to track the values of the parameter of interest over the process window decreases.

In a further aspect, the performance metrics can be compared with a given specification to determine whether the measurement is sufficiently accurate over the process window. In other words, at some point, measurement capability degrades so much that a change in any of the measurement model, metrology target, measurement system, or combination of metrology systems must be contemplated to bring the measurement capability within specification.

In the examples illustrated in FIGS. 4A-4C, the correlation coefficient, $R^2$, the slope, and the average offset are used as quantitative metrics of goodness of parameter tracking. However, these metrics are provided by way of non-limiting example. Many other quantitative performance metrics, or combinations of performance metrics, may be contemplated. In one example, three-sigma precision in the presence of random noise may be employed as a performance metric. In another example, derivatives of measured parameters with respect to under-layer thickness and/or optical properties may be employed to express measurement sensitivity to under-layers. In yet another example, average tool-to-tool matching of measured parameter values may be employed as a performance metric. In general, any suitable quantitative metric may be contemplated.

In block 206, the metric indicative of a parameter tracking performance of the metrology system is stored in a memory (e.g., memory 132 of computing system 130.

In another further aspect, the measurement model is parameterized by a process based principal component analysis (PCA) parameterization. Several examples of such a parameterization are described in U.S. Patent Publication No. 2013/0110477 by Stilian Pandev, the subject matter of which is incorporated herein by reference. A process based PCA parameterization effectively reduces the number of degree of freedom of the measurement model such that the model parameters can be effectively resolved from measurement data without excessive loss of measurement information.

Figure 5:
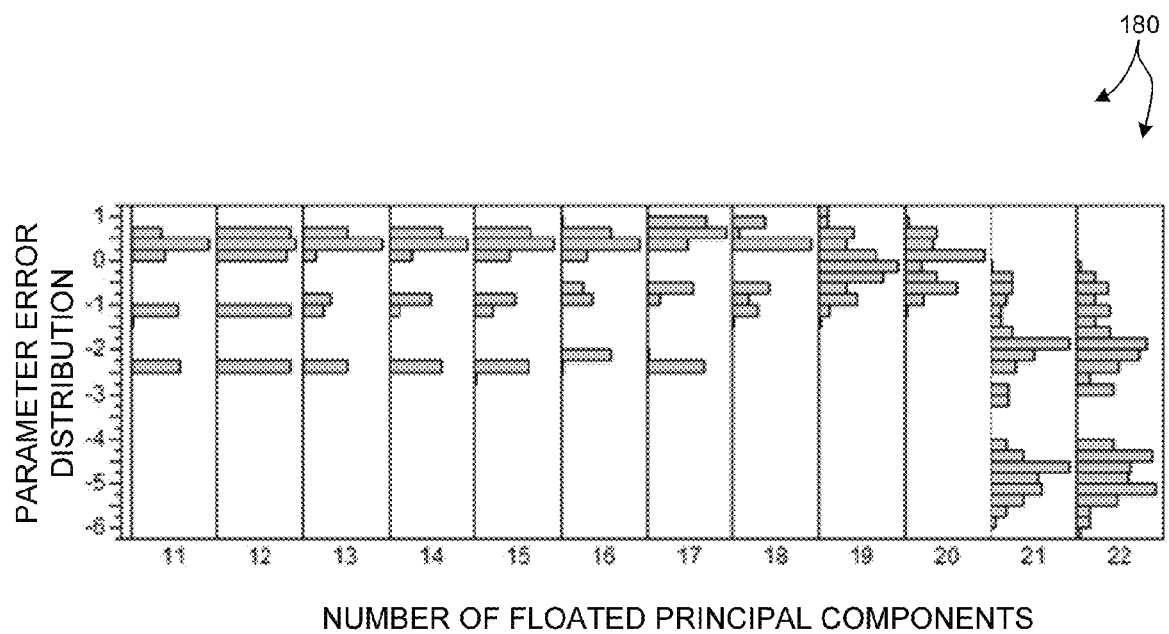
FIG. 5 illustrates a plot 180 of a series of probability distributions of estimation errors for a parameter of interest.

Typically, in a model-based measurement analysis, a decision must be made regarding which parameters to float and which parameters to constrain (e.g., fix to a particular value, or constrain by a particular function or range of values, etc.). PCA provides clear guidance regarding which principal component parameters to constrain. The inventors have discovered that while precision generally worsens with an increasing number of floated principal component parameters, tracking performance parameters, such as R2, usually reach an optimum at a particular number of floated principal component parameters. For example, FIG. 5 illustrates a plot 180 of a series of probability distributions of estimation errors for one of the parameters of interest. Each distribution corresponds to a different number of floated principal components. As depicted in FIG. 5, an optimum is reached around 19 or 20 floated principal components. If a smaller or larger number of principal components are floated, the tracking error distributions become worse. In this example, the optimum number of floated principal components is determined by random and systematic noise in the measured data. Using PCA in the context of the methods and systems described herein allows more parameters to be floated for a particular model, and provides clear guidance regarding which parameters to float. This contributes to stable and accurate results, as the best parameters to float are correctly identified.

In another further aspect, the methods and systems for evaluating the capability of a measurement system to track measurement parameters through a given process window as described herein are also applied to track process parameters of interest.

Figures 6, 7, 8:
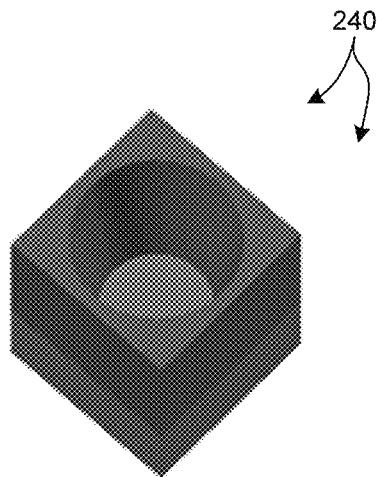
FIG. 6 is a diagram 240 illustrative of a simplified metrology model of a hole in an oxide layer subject to measurement by a two dimensional beam profile reflectometer (2-D BPR) system.
FIG. 7 is a table 245 illustrative of correlations between Height (H), Critical Dimension (CD) and Side Wall Angle (SWA) associated with the 2-D BPR measurement.
FIG. 8 is a table 250 illustrative of correlation between focus and exposure associated with the 2-D BPR measurement.

FIG. 6 is a diagram 240 illustrative of a simplified metrology model of a hole in an oxide layer subject to measurement by a two dimensional beam profile reflectometer (2-D BPR) system. Design of Experiments (DOE) simulation results demonstrate a high level of correlation between CD and SWA as illustrated in table 245 of FIG. 7. Thus, it is expected that the 2-D BPR measurement system would not be effective in distinguishing the two metrology parameters. However, in one example, lithography process parameters, focus setting and exposure dosage, were added to the measurement model, and tracked in accordance with the methods and systems described herein.

Figure 9A:
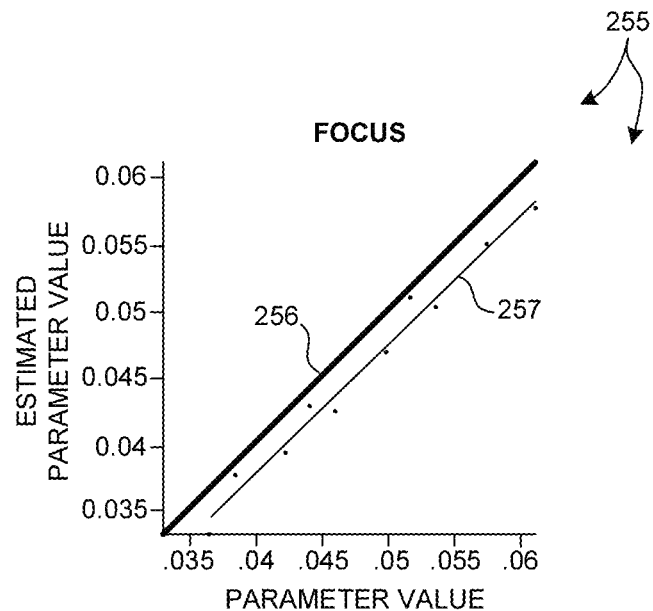
FIGS. 9A-9B illustrate plots 255 and 260 indicative of the tracking performance associated with 2-D BPR measurements of focus and exposure at two levels of perturbations, respectively.
Figure 9B:
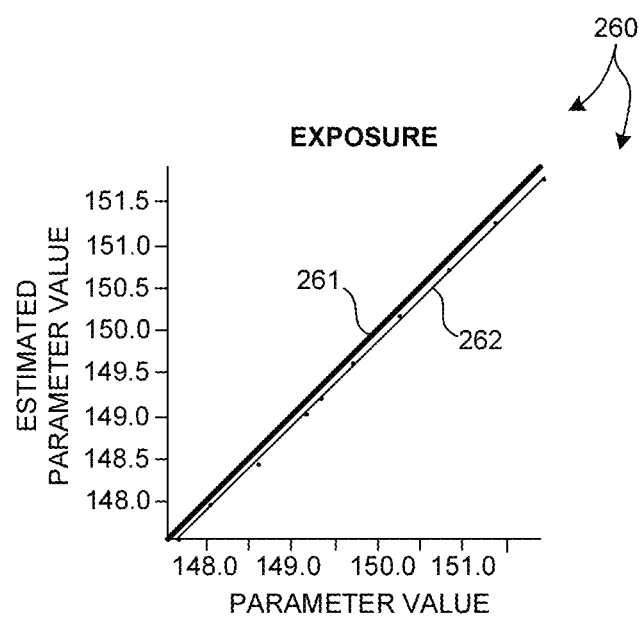

FIGS. 9A-9B illustrate the tracking performance associated with 2-D BPR measurements of focus and exposure, respectively, where the measurement model is parameterized by focus and exposure. FIG. 9A illustrates a plot 255 indicative of the tracking performance of the 2-D BPR measurement of focus employing the measurement model parameterized by focus and exposure. Line 256 indicates perfect tracking where the estimated parameter value is the same as the actual parameter value. Line 257 is a line representing a best fit among the illustrated data points. As illustrated in FIG. 9A, the tracking performance for focus is quite good. Similarly, FIG. 9B illustrates a plot 260 indicative of the tracking performance of the 2-D BPR measurement of exposure employing the measurement model parameterized by focus and exposure. Line 261 indicates perfect tracking where the estimated parameter value is the same as the actual parameter value. Line 262 is a line representing a best fit among the illustrated data points. As illustrated in FIG. 9B, the tracking performance for exposure is quite good. As illustrated in table 250 of FIG. 8, the correlation between focus and exposure is significantly less than the correlations among SWA and CD. Thus, the 2-D BPR measurement is able to resolve focus and exposure with greater success than CD and SWA.

In this manner, a measurement model is used to accurately track process parameters of interest (e.g. focus setting, exposure, etch time, deposition time, etc.).

In another further aspect, one or more metrics indicative of parameter tracking performance or precision are evaluated to determine whether changes to the measurement model, measurement targets, metrology system, or combination of metrology systems are required to improve parameter tracking performance.

Figure 15:
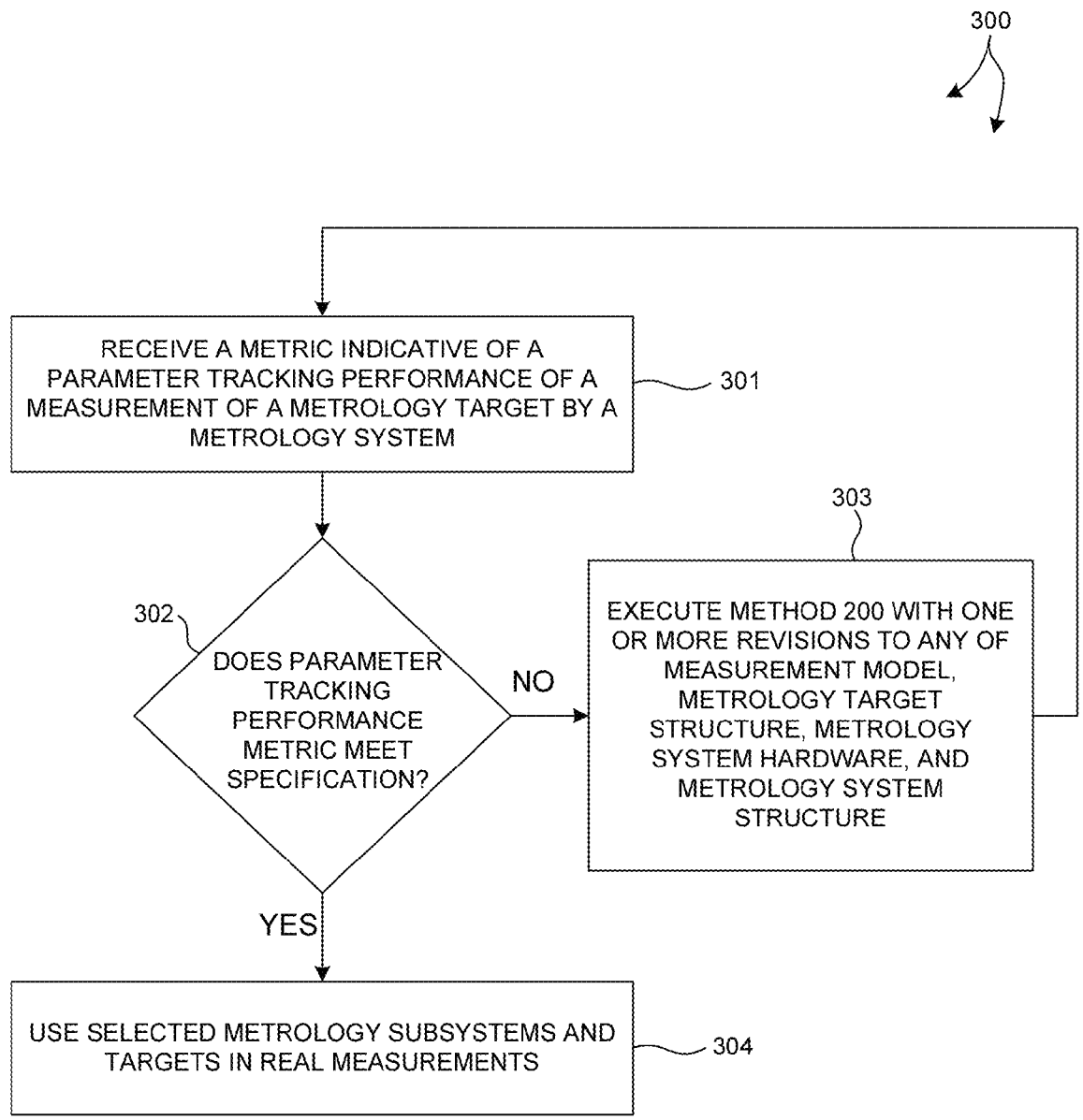
FIG. 15 is a flowchart illustrative of an exemplary method 300 suitable for implementation by the metrology system 100 of the present invention.

FIG. 15 illustrates a method 300 suitable for implementation by the metrology system 100 of the present invention. In one aspect, it is recognized that data processing blocks of method 300 may be carried out via a pre-programmed algorithm executed by one or more processors of computing system 130. While the following description is presented in the context of metrology system 100, it is recognized herein that the particular structural aspects of metrology system 100 do not represent limitations and should be interpreted as illustrative only.

In block 301, a metric indicative of a parameter tracking performance of a measurement of a metrology target by a metrology system is received. In one example, one or more performance metrics stored in block 206 of method 200 are retrieved from memory (e.g., memory 132).

In block 302, a determination is made whether the parameter tracking performance meets a specified requirement. If so, real measurements of the metrology target are performed by the metrology system as described in block 304. In some examples, these measurements are performed in a semiconductor production environment. If not, computing system 130 executes block 303.

In block 303, the elements of method 200 described with reference to FIG. 2, are executed with one or more revisions to any of 1) the measurement model, 2) the metrology target structure, 3) the metrology system hardware, and 4) the metrology system structure including multiple measurement modalities.

As described hereinbefore, a measurement model characterizes a response of a metrology system to a measurement of a metrology target. The measurement model includes one or more parameters of interest characterizing the metrology target and one or more system parameters characterizing the metrology system.

In some examples, the measurement model is modified by changing one or more parameters of interest characterizing the metrology target. This can be informed by the analysis described herein. For example, if the analysis shows that one or more parameters do not track well in the face of parameter variations, a change in those parameters may improve tracking performance. In another example, a change in the parameters of interest that are floated in a regression analysis is made to improve parameter tracking.

In another example, the measurement model is modified by changing one or more parameters of interest characterizing the metrology system. In some examples, a particular metrology tool operating configuration (e.g., measurement recipe) includes particular ranges of values such as illumination wavelengths, polarizations, angles of incidence, etc.). If the analysis described with reference to method 200 of FIG. 2 shows that one or more parameters do not track well in the face of parameter variations, a change in system parameter values may improve tracking performance. For example, tracking may improve by adding more measurement information (e.g., more illumination wavelengths, more polarizations (or Mueller matrix elements), more angles of incidence, more Fourier modes, more image pixels in a BPR system etc.). In this manner, the metrology tool operating configuration may be optimized based on the analysis described herein. In these examples, a particular metrology system architecture is presumed, and particular ranges of operating parameters are selected to realize optimal measurement capability.

In yet another example, the structure of one or more metrology targets on which the measurements are performed is optimized based on the analysis described with reference to method 200 of FIG. 2. In some examples, both primary metrology targets and secondary metrology targets are optimized in a multi-target metrology implementation. In some embodiments, special metrology targets with field enhancement elements (FEEs) can be designed to enhance sensitivity to parameters that need to be measured and/or reduce correlation with other parameters. Some examples are described by Jonathan M. Madsen et al., in U.S. Patent Publication No. 2013/0222795, entitled "Optical Metrology Using Targets With Field Enhancement Elements," the subject matter of which is incorporated herein by reference in its entirety.

Figure 10:
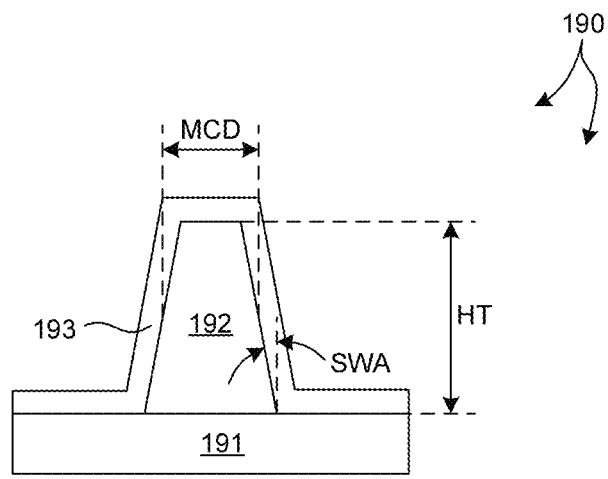
FIG. 10 illustrates a semiconductor structure including a photoresist trapezoid structure and a liner layer as a field enhancement element.

FIG. 10 illustrates a semiconductor structure 190 including a silicon base layer 190, a resist trap structure 192, and a liner layer 193 deposited over the silicon base layer 191 and resist trap structure 192. In this embodiment, liner layer 193 is used as FEE.

Figure 11:
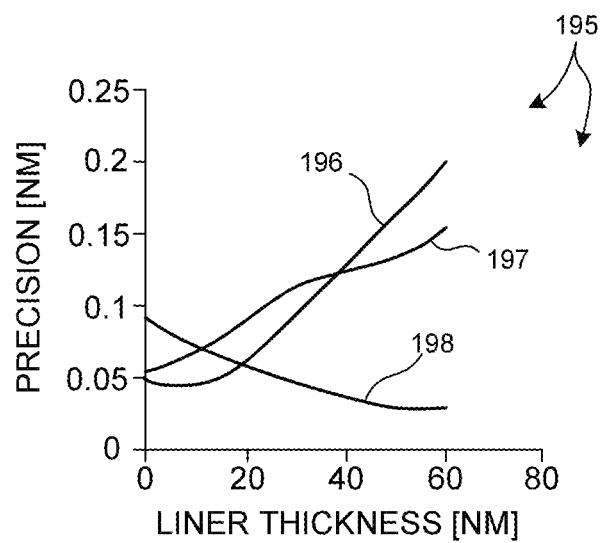
FIG. 11 illustrates a plot of the measurement precision achieved for three different parameters of interest for different liner layer thicknesses.

In one example, the thickness of the liner layer 193 is optimized to improve the measurement precision of the measurement parameters of the resist trap structure. FIG. 11 illustrates a plot 195 of the measurement precision achieved for three different parameters of interest (MCD, SWA, and HT) for different liner thicknesses. Plotline 196 illustrates the measurement precision achieved in the measurement of MCD for different liner thicknesses. Plotline 197 illustrates the measurement precision achieved in the measurement of SWA for different liner thicknesses. Plotline 198 illustrates the measurement precision achieved in the measurement of HT for different liner thicknesses. As illustrated in FIG. 11, the measurement precision of SWA degrades with increasing liner thickness. In other words, it would be preferable not to introduce a liner for purposes of measuring SWA only. However, the measurement precision of HT improves with increasing liner thickness, so it would be preferable to have a thick liner for purposes of measuring HT only. The measurement of precision of MCD initially improves up to a liner thickness of approximately 10 nanometers and then degrades with further increases in liner thickness. Based on the analysis of measurement precision using the methods described herein, the trade-offs introduced by a FEE such as liner 192 become clear. For example, one may choose a liner thickness of approximately 20 nanometers as a compromise to provide the optimum measurement precision for MCD, SWA, and HT of resist structure 193.

In another example, the thickness of the liner layer 193 is optimized to improve the tracking capability of the measurement parameters of the resist trap structure.

Figure 12A:
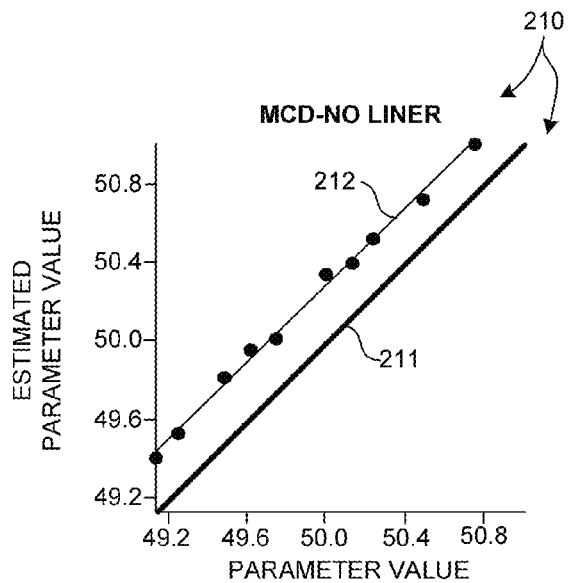
FIGS. 12A-12B illustrate plots of estimated values of middle critical dimension (MCD) over a process window without a liner layer and with a liner layer, respectively.
Figure 12B:
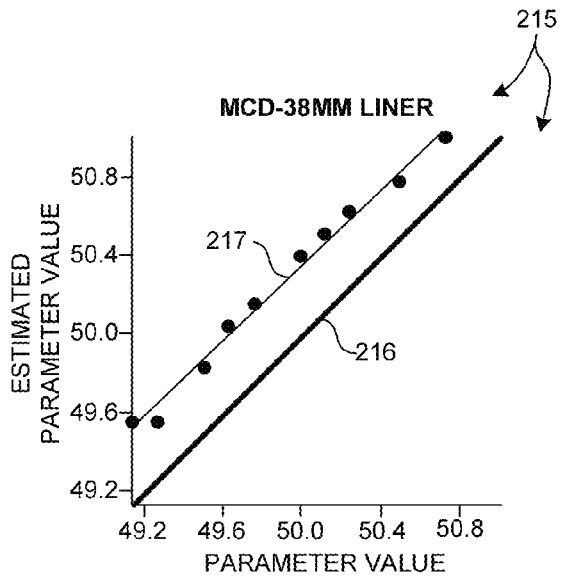

FIG. 12A illustrates a plot 210 including a best fit line 212 of the estimated parameter values of MCD over a process window and a line 211 of known parameter values of MCD over the same process window for a resist structure 192 without a liner layer 193. FIG. 12B illustrates a plot 215 including a best fit line 217 of the estimated parameter values of MCD over the process window and a line 216 of the known parameter values of MCD over the same process window for a liner layer 193 with a thickness of 38 nanometers.

Figure 13A:
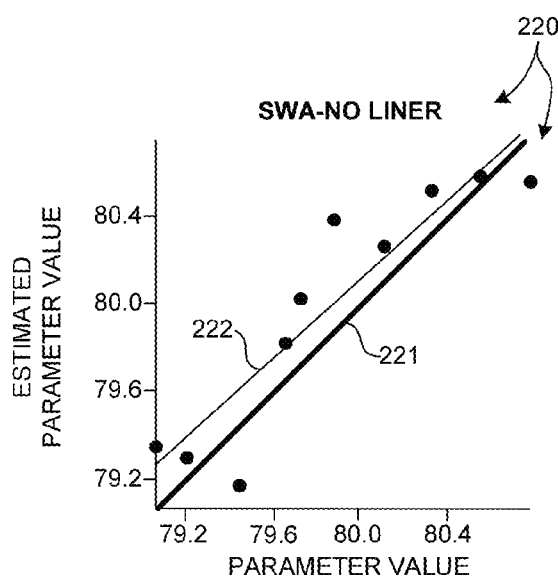
FIGS. 13A-13B illustrate plots of estimated values of sidewall angle (SWA) over a process window without a liner layer and with a liner layer, respectively.
Figure 13B:
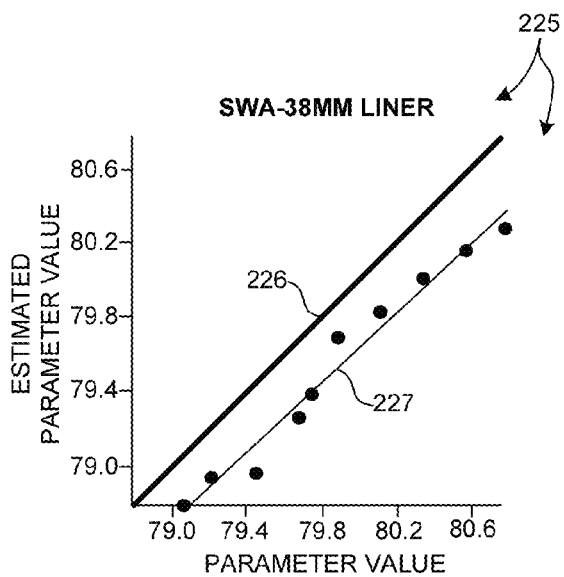

FIG. 13A illustrates a plot 220 including a best fit line 222 of the estimated parameter values of SWA over a process window and a line 221 of known parameter values of SWA over the same process window for a resist structure 192 without a liner layer 193. FIG. 13B illustrates a plot 225 including a best fit line 227 of the estimated parameter values of SWA over the process window and a line 226 of known parameter values of SWA over the same process window for a liner layer 193 with a thickness of 38 nanometers.

Figure 14A:
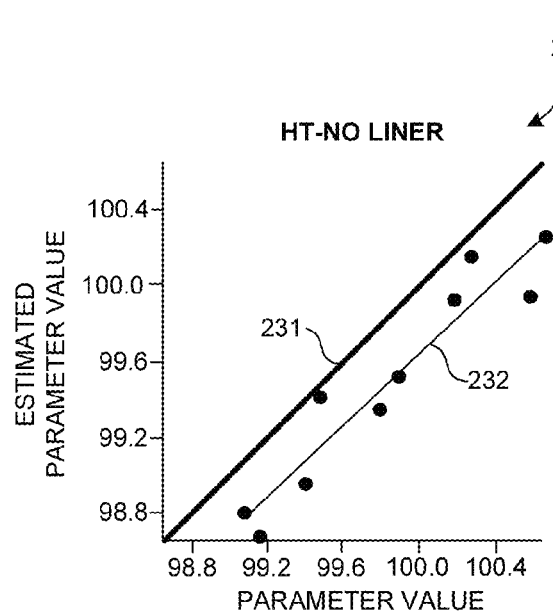
FIGS. 14A-14B illustrate plots of estimated values of height (HT) over a process window without a liner layer and with a liner layer, respectively.
Figure 14B:
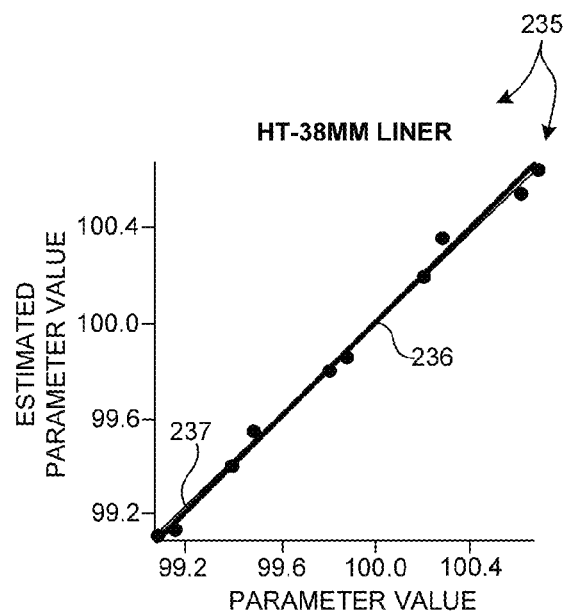

FIG. 14A illustrates a plot 230 including a best fit line 232 of the estimated parameter values of HT over a process window and a line 231 of known parameter values of HT over the same process window for a resist structure 192 without a liner layer 193. FIG. 14B illustrates a plot 235 including a best fit line 237 of the estimated parameter values of HT over the process window and a line 236 of known parameter values of HT over the same process window for a liner layer 193 with a thickness of 38 nanometers.

As depicted in FIGS. 12A-12B, 13A-13B, and 14A-14B, the parameter tracking capability of the measurement system is slightly degraded for MCD and SWA with the introduction of the 38 millimeter thick liner layer. However, the parameter tracking capability of the measurement system for HT is significantly improved with the introduction of the liner layer with 38 millimeter thickness.

In yet another example, the configuration or design of a metrology tool (e.g., metrology system hardware, measurement technology, etc.) is optimized based on the analysis. This can be informed by the analysis described herein. For example, if the analysis shows that one or more parameters do not track well in the face of parameter variations, a change metrology system architecture or design may improve tracking performance. The analysis can executed again with the changed system architecture or design to confirm that parameter tracking capability has improved and meets specification.

In yet another example, the metrology system includes multiple measurement modalities. In other words, the metrology system employs more than one measurement technique, e.g., x-ray reflectance and spectroscopic ellipsometry, etc. In some examples, the number and types of different measurement modalities is optimized based on the analysis described herein. For example, if the analysis shows that one or more parameters do not track well in the face of parameter variations, a change the number and/or type of measurement modalities may improve tracking performance. The analysis can executed again with the modified selection of metrology subsystems to confirm that parameter tracking capability has improved and meets specification. Moreover, the relative weights of the different metrology subsystems or measurement modalities may be optimized to obtain the best value of the merit function. While any single measurement technology alone may not be optimal, there is no reason why two such technologies should have equal contributions to achieve the best result.

In general, the optimization can include changes to more than one element of the measurement. Any combination of changes to the measurement model, the metrology target structure, the metrology system hardware, and the metrology system structure including multiple measurement modalities may be contemplated, and the impact on parameter tracking due to these changes can be evaluated in accordance with the methods and systems described herein.

As depicted in FIG. 15, elements 301, 302, and 303 may be iterated until parameter tracking performance reaches specification. In some examples, the space of measurement model parameters, target design parameters, metrology system types, or combinations of metrology systems is sampled and method 200 is repeatedly executed for each different system configuration to calculate tracking metrics that are used for visualization or data analysis. This process can be executed as part of an automatic optimization (e.g. non-linear regression) on continuous system parameters to produce an optimal design of the metrology system and measurement recipe. For multiple discrete choices (e.g., selection among multiple possible metrology subsystems), an exhaustive search may be performed among all possible configurations. An optimal configuration can be automatically selected. Many different global optimization algorithms including simulated annealing, evolutionary algorithms, or others, may be contemplated to automate all or part of the optimization process to reach a satisfactory combination of measurement model, the metrology target structure, metrology system hardware, and metrology system structure including multiple measurement modalities to meet the measurement objective.

In general, the systems and methods described herein can be implemented as part of the process of preparing a measurement model and metrology system for off-line or on-tool measurement. In addition, both measurement models and any reparameterized measurement model may describe one or more target structures and measurement sites.

In some examples, the methods described herein are implemented as an element of a SpectraShape® optical critical-dimension metrology system available from KLA-Tencor Corporation, Milpitas, Calif., USA. In this manner, the measurement model and system configuration is created and ready for use immediately.

In some other examples, the methods described herein are implemented off-line, for example, by a computing system implementing AcuShape® software available from KLA-Tencor Corporation, Milpitas, Calif., USA. The resulting measurement model and system configuration may be incorporated as an element of an AcuShape® library that is accessible by a metrology system performing measurements.

In general, any measurement technique (i.e., measurement modality), or combination of two or more measurement techniques may be contemplated within the scope of this patent document. Exemplary measurement techniques include, but are not limited to spectroscopic ellipsometry, including Mueller matrix ellipsometry, spectroscopic reflectometry, spectroscopic scatterometry, scatterometry overlay, beam profile reflectometry, both angle-resolved and polarization-resolved, beam profile ellipsometry, single or multiple discrete wavelength ellipsometry, transmission small angle x-ray scatterometer (TSAXS), small angle x-ray scattering (SAXS), grazing incidence small angle x-ray scattering (GISAXS), wide angle x-ray scattering (WAXS), x-ray reflectivity (XRR), x-ray diffraction (XRD), grazing incidence x-ray diffraction (GIXRD), high resolution x-ray diffraction (HRXRD), x-ray photoelectron spectroscopy (XPS), x-ray fluorescence (XRF), grazing incidence x-ray fluorescence (GIXRF), low-energy electron induced x-ray emission scatterometry (LEXES), x-ray tomography, and x-ray ellipsometry. In general, any metrology technique applicable to the characterization of semiconductor structures, including image based metrology techniques, may be contemplated. Additional sensor options include electrical sensors such as non-contact capacitance/voltage or current/voltage sensors which bias the device and detect the resulting bias with an optical sensor (or the converse), or assisted optical techniques, such as XRD, XRF, XPS, LEXES, SAXS, and pump probe techniques. In one embodiment a two-dimensional beam profile reflectometer (pupil imager) may be used to collect both angle resolved and/or multi-spectral data in a small spot size. A UV Linnik interferometer may also be used as a Mueller matrix spectral pupil imager.

Although several exemplary process parameters are described hereinbefore with reference to lithography and associated focus and exposure metrologies, the methods and systems described herein may involve other process models (e.g., etch or deposition processing), and other metrologies (e.g., etch and deposition metrologies). The methods and systems described herein may also involve other reference metrology technologies (e.g. SEM, TEM, AFM, X-ray). Moreover, the methods and systems described herein are discussed with reference to optical metrology systems (e.g., spectroscopic ellipsometers, reflectometers, BPR systems, etc.), but can be also applied to other model-based metrologies (e.g., overlay, CD-SAXS, XRR, etc.).

In yet another aspect, the measurement analysis described herein can be used to provide active feedback to a process tool (e.g., lithography tool, etch tool, deposition tool, etc.). For example, values of the depth and focus parameters determined using the methods described herein can be communicated to the lithography tool to adjust the lithography system to achieve a desired output. In a similar way etch parameters (e.g., etch time, diffusivity, etc.) or deposition parameters (e.g., time, concentration, etc.) may be included in the integrated measurement model to provide active feedback to etch tools or deposition tools, respectively.

As described herein, the term "critical dimension" includes any critical dimension of a structure (e.g., bottom critical dimension, middle critical dimension, top critical dimension, sidewall angle, grating height, etc.), a critical dimension between any two or more structures (e.g., distance between two structures), and a displacement between two or more structures (e.g., overlay displacement between overlaying grating structures, etc.). Structures may include three dimensional structures, patterned structures, overlay structures, etc.

As described herein, the term "critical dimension application" or "critical dimension measurement application" includes any critical dimension measurement.

As described herein, the term "metrology system" includes any system employed at least in part to characterize a specimen in any aspect, including measurement applications such as critical dimension metrology, overlay metrology, focus/dosage metrology, and composition metrology. However, such terms of art do not limit the scope of the term "metrology system" as described herein. In addition, the metrology system 100 may be configured for measurement of patterned wafers and/or unpatterned wafers. The metrology system may be configured as a LED inspection tool, edge inspection tool, backside inspection tool, macro-inspection tool, or multi-mode inspection tool (involving data from one or more platforms simultaneously), and any other metrology or inspection tool that benefits from the calibration of system parameters based on critical dimension data.

Various embodiments are described herein for a semiconductor processing system (e.g., an inspection system or a lithography system) that may be used for processing a specimen. The term "specimen" is used herein to refer to a wafer, a reticle, or any other sample that may be processed (e.g., printed or inspected for defects) by means known in the art.

As used herein, the term "wafer" generally refers to substrates formed of a semiconductor or non-semiconductor material. Examples include, but are not limited to, monocrystalline silicon, gallium arsenide, and indium phosphide. Such substrates may be commonly found and/or processed in semiconductor fabrication facilities. In some cases, a wafer may include only the substrate (i.e., bare wafer). Alternatively, a wafer may include one or more layers of different materials formed upon a substrate. One or more layers formed on a wafer may be "patterned" or "unpatterned." For example, a wafer may include a plurality of dies having repeatable pattern features.

A "reticle" may be a reticle at any stage of a reticle fabrication process, or a completed reticle that may or may not be released for use in a semiconductor fabrication facility. A reticle, or a "mask," is generally defined as a substantially transparent substrate having substantially opaque regions formed thereon and configured in a pattern. The substrate may include, for example, a glass material such as amorphous $SiO_2$. A reticle may be disposed above a resist-covered wafer during an exposure step of a lithography process such that the pattern on the reticle may be transferred to the resist.

One or more layers formed on a wafer may be patterned or unpatterned. For example, a wafer may include a plurality of dies, each having repeatable pattern features. Formation and processing of such layers of material may ultimately result in completed devices. Many different types of devices may be formed on a wafer, and the term wafer as used herein is intended to encompass a wafer on which any type of device known in the art is being fabricated.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. A method comprising:
   receiving a measurement model characterizing a response of a metrology system to a measurement of a metrology target onto a computing system, wherein the measurement model includes one or more parameters of interest characterizing the metrology target and one or more system parameters characterizing the metrology system, the computing system configured to:
   determine a set of known values associated with any of the one or more parameters of interest that span a desired process window associated with the metrology target;
   determine a set of perturbed synthetic measurement signals based on a set of simulations of the measurement model characterizing a set of measurements of the metrology target for each of the set of known values of any of the one or more parameters of interest and at least one perturbation signal;

determine estimated values associated with each of the one or more parameters of interest based on the set of perturbed synthetic measurement signals;

determine a metric indicative of a parameter tracking performance of the metrology system based on the estimated values associated with each of the one or more parameters of interest and the known values associated with each of the one or more parameters of interest; and store the metric in a memory.

2. The method of claim 1, wherein the at least one perturbation signal is indicative of a systematic perturbation of the metrology system.

3. The method of claim 1, wherein the at least one perturbation signal is indicative of a random perturbation of the metrology system.

4. The method of claim 1, further comprising:
changing a parameterization of the measurement model based on a value of the metric indicative of a parameter tracking performance of the metrology system.

5. The method of claim 1, further comprising:
changing a metrology target structure based on a value of the metric indicative of a parameter tracking performance of the metrology system.

6. The method of claim 1, further comprising:
changing a structure of the metrology system based on a value of the metric indicative of a parameter tracking performance of the metrology system.

7. The method of claim 1, further comprising:
changing a combination of measurement modalities of the metrology system based on a value of the metric indicative of a parameter tracking performance of the metrology system.

8. The method of claim 1, wherein the determining of the estimated values associated with each of the one or more parameters of interest based on the set of synthetic measurement signals involves transforming the measurement model parameterization to a set of principal components.

9. The method of claim 1, wherein at least one of the parameters of interest is a process parameter.

10. The method of claim 1, wherein the determining the estimated values associated with each of the one or more parameters of interest involves a non-linear regression of the measurement model.

11. A metrology system comprising:
an illumination source;
a detector; and
a computing system configured to
receive a measurement model characterizing a response of a metrology system to a measurement of a metrology target, wherein the measurement model includes one or more parameters of interest characterizing the metrology target and one or more system parameters characterizing the metrology system;
determine a set of known values associated with any of the one or more parameters of interest that span a desired process window associated with the metrology target;
determine a set of perturbed synthetic measurement signals based on a set of simulations of the measurement model characterizing a set of measurements of the metrology target for each of the set of known values of any of the one or more parameters of interest and at least one perturbation signal;
determine estimated values associated with each of the one or more parameters of interest based on the set of perturbed synthetic measurement signals;
determine a metric indicative of a parameter tracking performance of the metrology system based on the estimated values associated with each of the one or more parameters of interest and the known values associated with each of the one or more parameters of interest; and
store the metric in a memory.

12. The metrology system of claim 11, wherein the computing system is further configured to:
change a parameterization of the measurement model based on a value of the metric indicative of a parameter tracking performance of the metrology system.

13. The metrology system of claim 11, wherein the computing system is further configured to:
change a metrology target structure based on a value of the metric indicative of a parameter tracking performance of the metrology system.

14. The metrology system of claim 11, wherein the computing system is further configured to:
change a structure of the metrology system based on a value of the metric indicative of a parameter tracking performance of the metrology system.

15. The metrology system of claim 11, wherein the computing system is further configured to:
change a combination of measurement modalities of the metrology system based on a value of the metric indicative of a parameter tracking performance of the metrology system.

16. The metrology system of claim 11, wherein the determining of the estimated values associated with each of the one or more parameters of interest based on the set of synthetic measurement signals involves transforming the measurement model parameterization to a set of principal components.

17. A metrology system comprising:
a computing system; and
a non-transitory, computer-readable medium including, code for causing the computing system to:
receive a measurement model characterizing a response of a metrology system to a measurement of a metrology target, wherein the measurement model includes one or more parameters of interest characterizing the metrology target and one or more system parameters characterizing the metrology system;
determine a set of known values associated with any of the one or more parameters of interest that span a desired process window associated with the metrology target;
determine a set of perturbed synthetic measurement signals based on a set of simulations of the measurement model characterizing a set of measurements of the metrology target for each of the set of known values of any of the one or more parameters of interest and at least one perturbation signal;
determine estimated values associated with each of the one or more parameters of interest based on the set of perturbed synthetic measurement signals;
determine a metric indicative of a parameter tracking performance of the metrology system based on the estimated values associated with each of the one or more parameters of interest and the known values associated with each of the one or more parameters of interest; and
store the metric in a memory.

18. The metrology system of claim 17, wherein the determining of the estimated values associated with each of the one or more parameters of interest based on the set of synthetic measurement signals involves transforming the measurement model parameterization to a set of principal components.

19. The metrology system of claim 17, wherein at least one of the parameters of interest is a process parameter.

20. The metrology system of claim 17, wherein the determining the estimated values associated with each of the one or more parameters of interest involves a non-linear regression of the measurement model.

* * * * *